(12) United States Patent
Shimase et al.

(10) Patent No.: US 10,138,456 B2
(45) Date of Patent: Nov. 27, 2018

(54) CELL CONCENTRATION ADJUSTMENT DEVICE, AND AUTOMATIC SUBCULTURE SYSTEM USING SAME

(71) Applicant: HITACHI HIGH-TECHNOLOGIES CORPORATION, Minato-ku, Tokyo (JP)

(72) Inventors: Akihiro Shimase, Tokyo (JP); Kazumichi Imai, Tokyo (JP); Sadamitsu Aso, Tokyo (JP); Eiichiro Takada, Tokyo (JP); Masako Kawarai, Tokyo (JP); Toshinari Sakurai, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 15/327,208

(22) PCT Filed: Jul. 8, 2015

(86) PCT No.: PCT/JP2015/069616
§ 371 (c)(1),
(2) Date: Jan. 18, 2017

(87) PCT Pub. No.: WO2016/013394
PCT Pub. Date: Jan. 28, 2016

(65) Prior Publication Data
US 2017/0159003 A1   Jun. 8, 2017

(30) Foreign Application Priority Data

Jul. 22, 2014  (JP) ................................ 2014-148636

(51) Int. Cl.
*C12M 1/00* (2006.01)
*C12M 3/00* (2006.01)
(Continued)

(52) U.S. Cl.
CPC ............ *C12M 41/40* (2013.01); *C12M 23/58* (2013.01); *C12M 27/00* (2013.01); *C12M 29/14* (2013.01);
(Continued)

(58) Field of Classification Search
CPC ...... C12M 47/00; C12M 47/02; C12M 47/04; C12M 47/10; C12M 47/12
See application file for complete search history.

(56) References Cited

U.S. PATENT DOCUMENTS

2004/0229349 A1* 11/2004 Daridon ................... C12M 1/34
435/305.2
2009/0081770 A1* 3/2009 Srienc .................... C12M 47/04
435/289.1

FOREIGN PATENT DOCUMENTS

JP       3-131743 A     6/1991
JP     2005-198626 A    7/2005
(Continued)

OTHER PUBLICATIONS

English translation of JP 2005-198626, Harada et al, 2018.*

*Primary Examiner* — Nathan A Bowers
(74) *Attorney, Agent, or Firm* — Miles & Stockbridge P.C.

(57) ABSTRACT

A device which automatically performs a step in which expanded and cultured cells are diluted to a desired cell concentration and re-inoculated using a cell-concentration adjustment device having an inlet for taking in a cell suspension; an outlet for discharging a diluted cell suspension; and a flow path which is provided between the inlet and the outlet and is capable of holding a cell suspension, the flow path being provided with: a liquid delivery pump for causing a cell suspension inside to flow; a cell-concentration measurement instrument for collecting data related to a cell concentration per unit amount of the cell suspension; and a
(Continued)

dilution-liquid container for holding a dilution liquid which is supplied to the flow path to dilute the cell suspension. The device further includes a control unit for controlling at least the liquid delivery pump on the basis of the data obtained by the cell-concentration measurement instrument, wherein the control unit determines, on the basis of the data obtained by the cell-concentration measurement instrument, an amount of the dilution liquid required to bring the cell concentration to the desired concentration, and drives the liquid delivery pump so as to take in the required amount of the dilution liquid into the flow path and mix the cell suspension and the dilution liquid.

8 Claims, 10 Drawing Sheets

(51) Int. Cl.
*C12M 1/34* (2006.01)
*C12M 1/02* (2006.01)
*C12M 1/36* (2006.01)
*C12Q 1/06* (2006.01)

(52) U.S. Cl.
CPC ............ *C12M 29/18* (2013.01); *C12M 31/10* (2013.01); *C12M 41/06* (2013.01); *C12M 41/36* (2013.01); *C12M 41/48* (2013.01); *C12Q 1/06* (2013.01)

(56) References Cited

FOREIGN PATENT DOCUMENTS

| | | |
|---|---|---|
| JP | 2007-185165 A | 7/2007 |
| JP | 2008-79554 A | 4/2008 |
| JP | 2009-525756 A | 7/2009 |
| WO | WO 2006/107684 A2 | 10/2006 |
| WO | WO 2007/092571 A2 | 8/2007 |
| WO | WO 2012/000102 A1 | 1/2012 |

* cited by examiner

[FIG. 1]
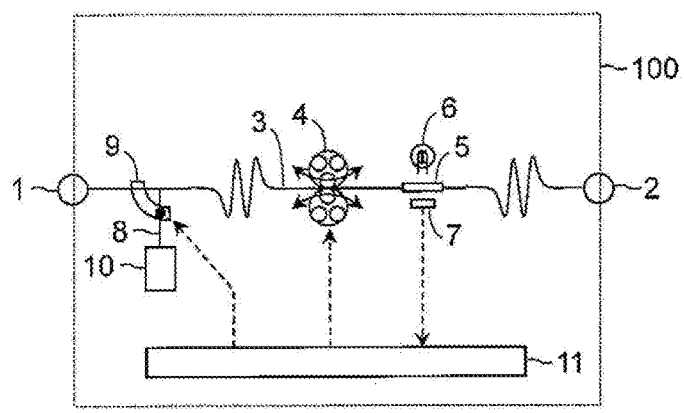
[FIG. 2]
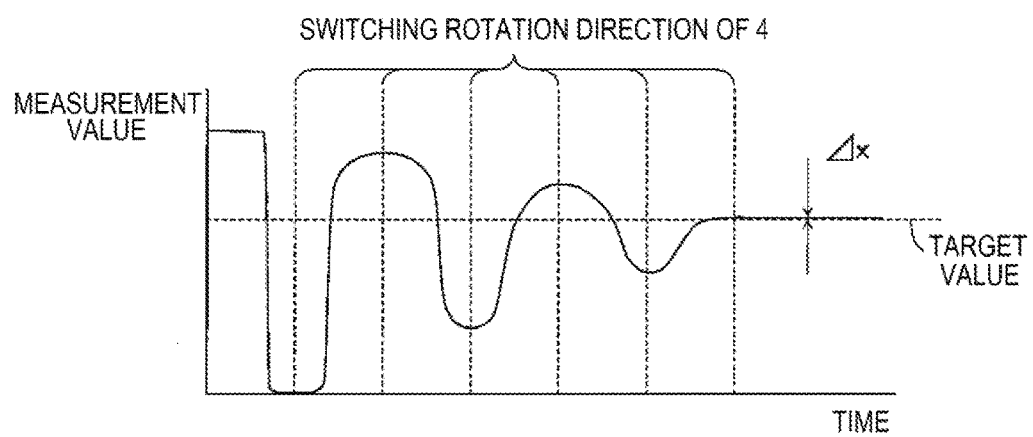

[FIG. 3]
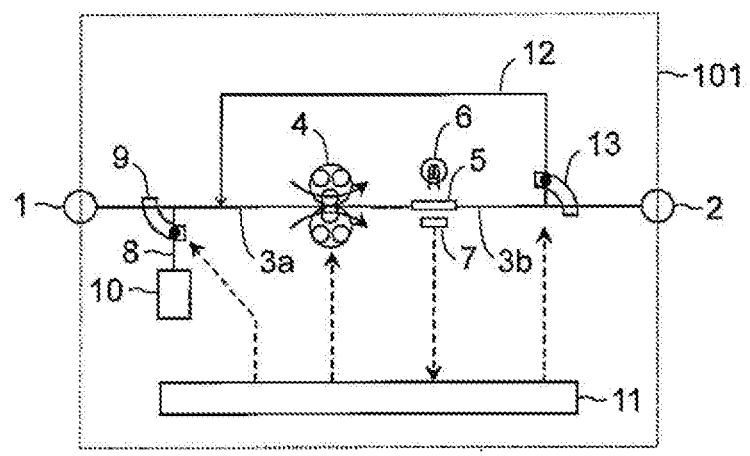
[FIG. 4]
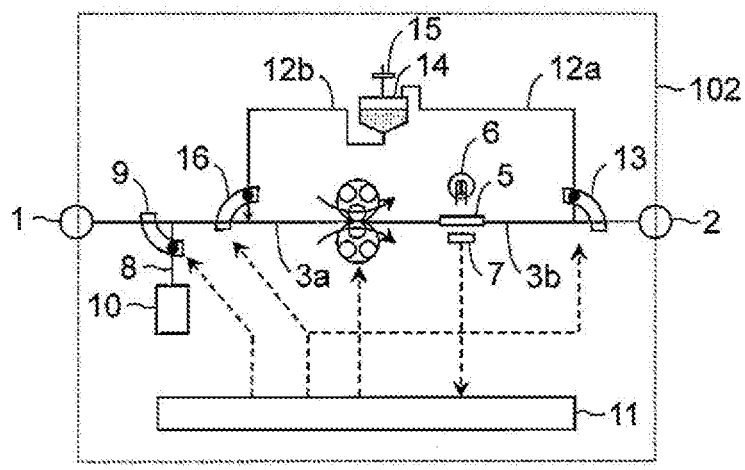

[FIG. 5]
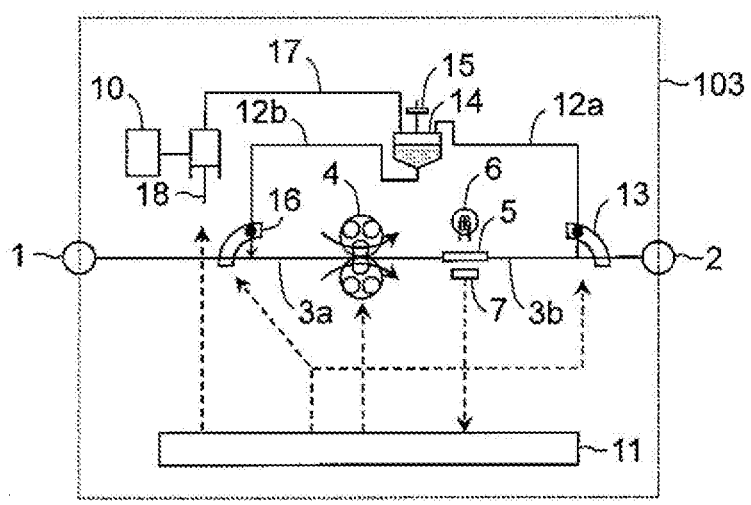

[FIG. 6]
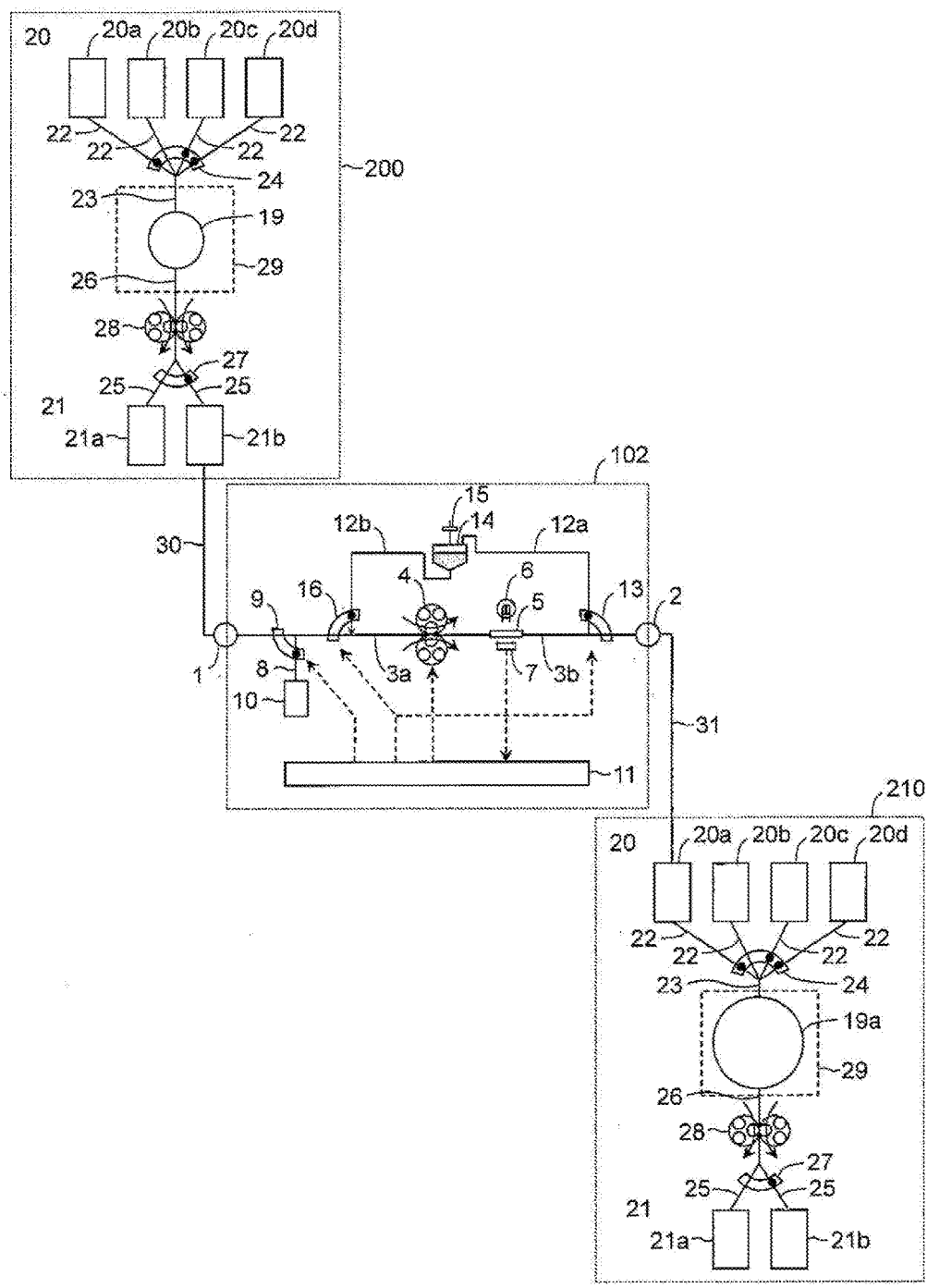

[FIG. 7]
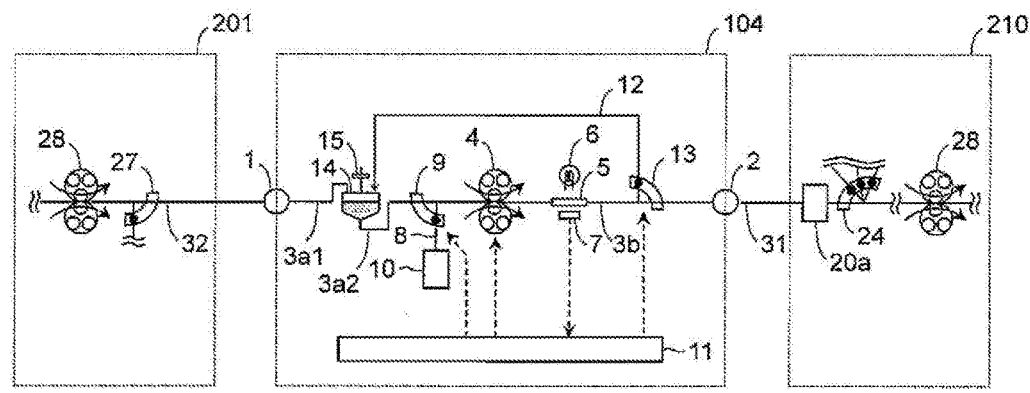
[FIG. 8]
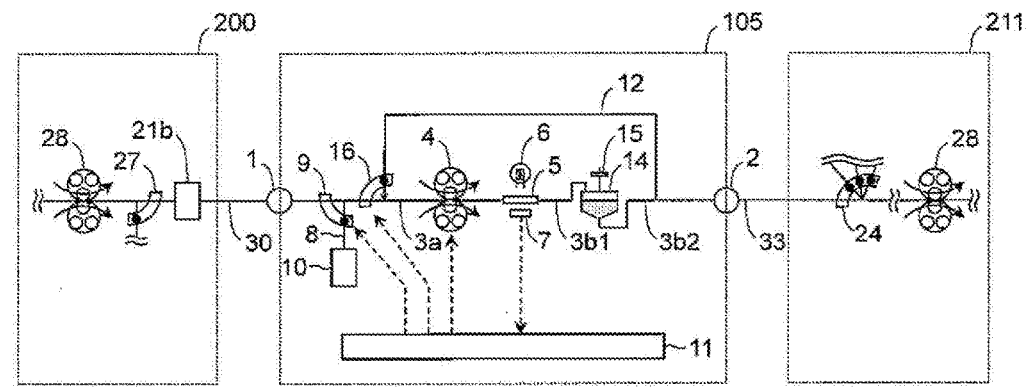

[FIG. 9]
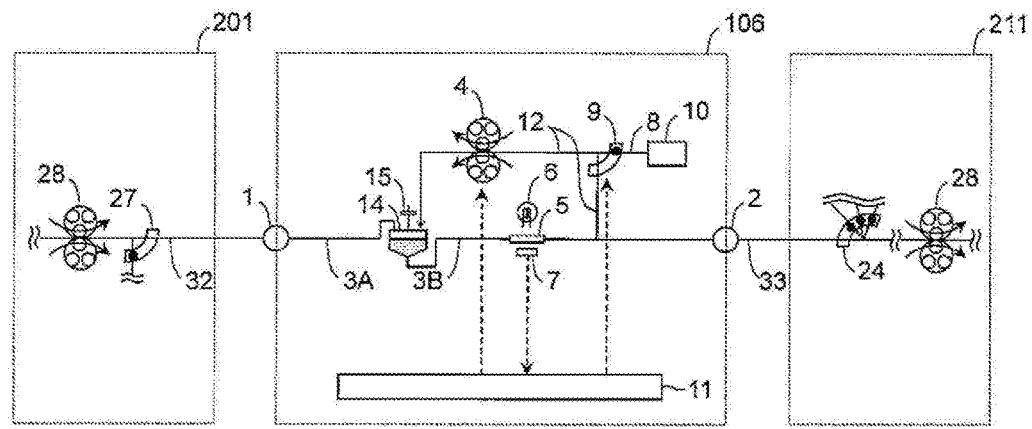
[FIG. 10]
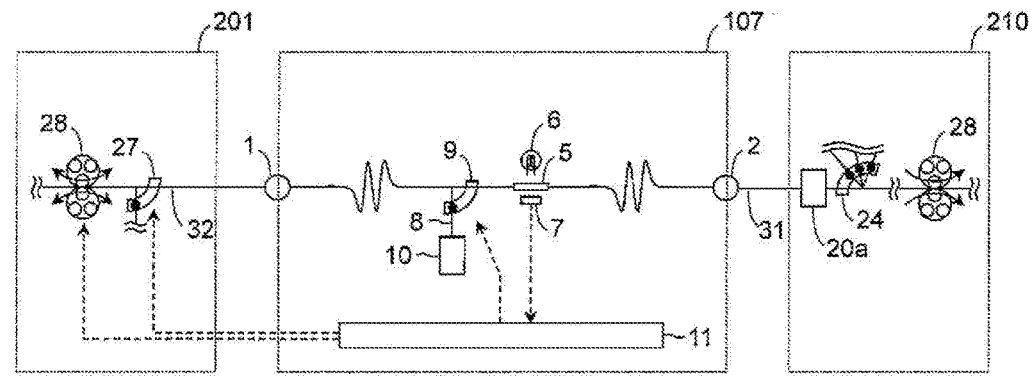

[FIG. 11]
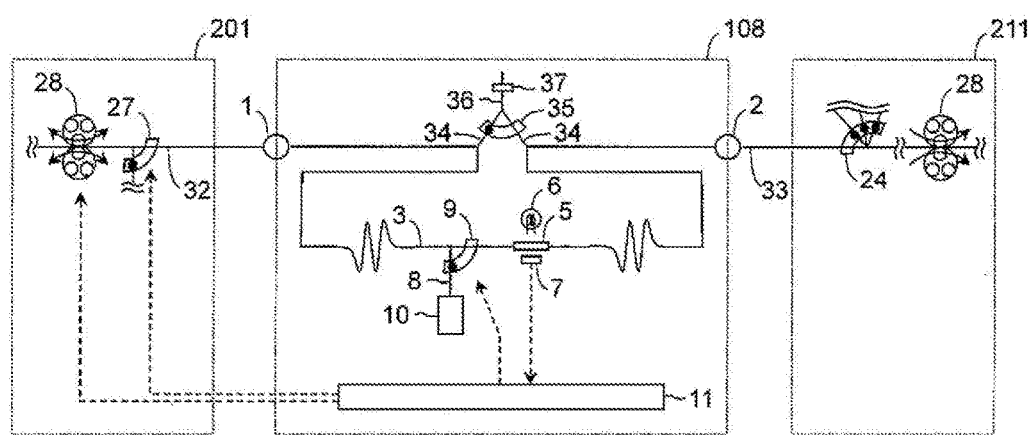

[FIG. 12]
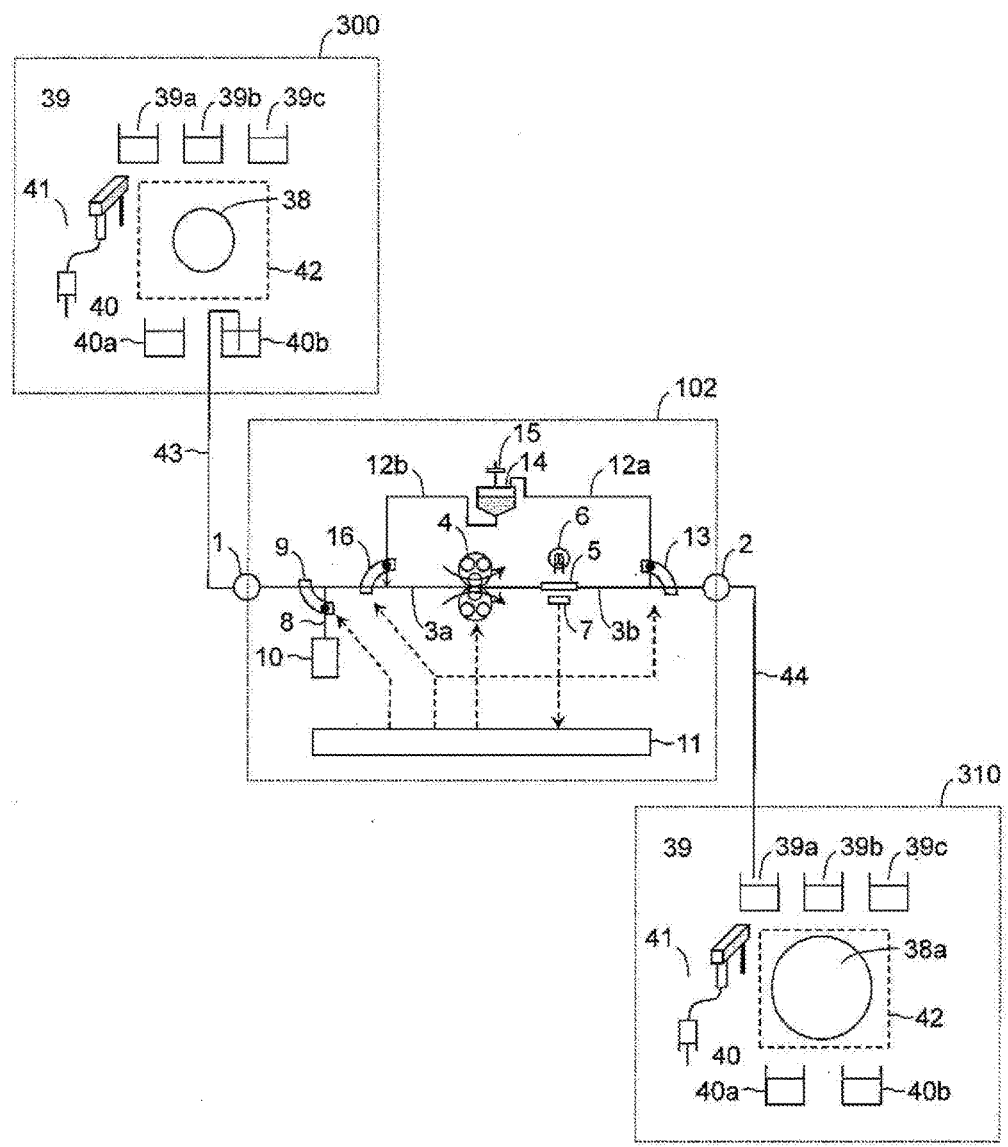

[FIG. 13]
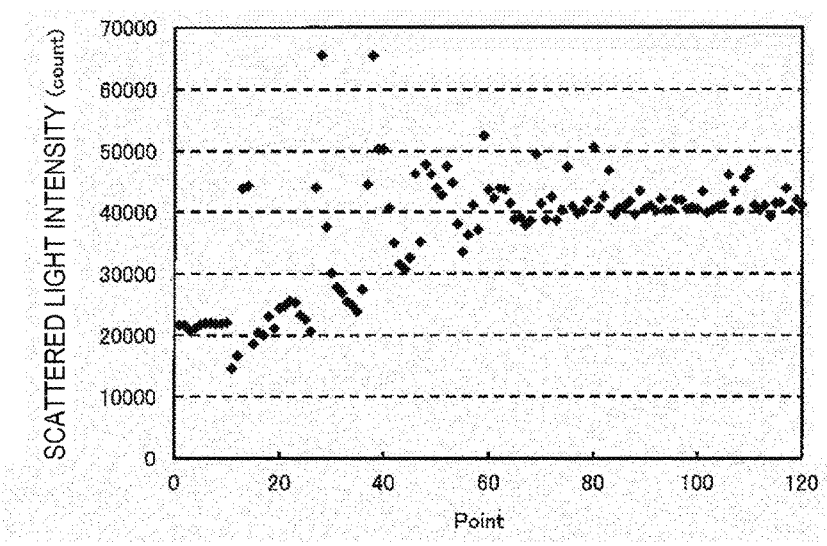
[FIG. 14]
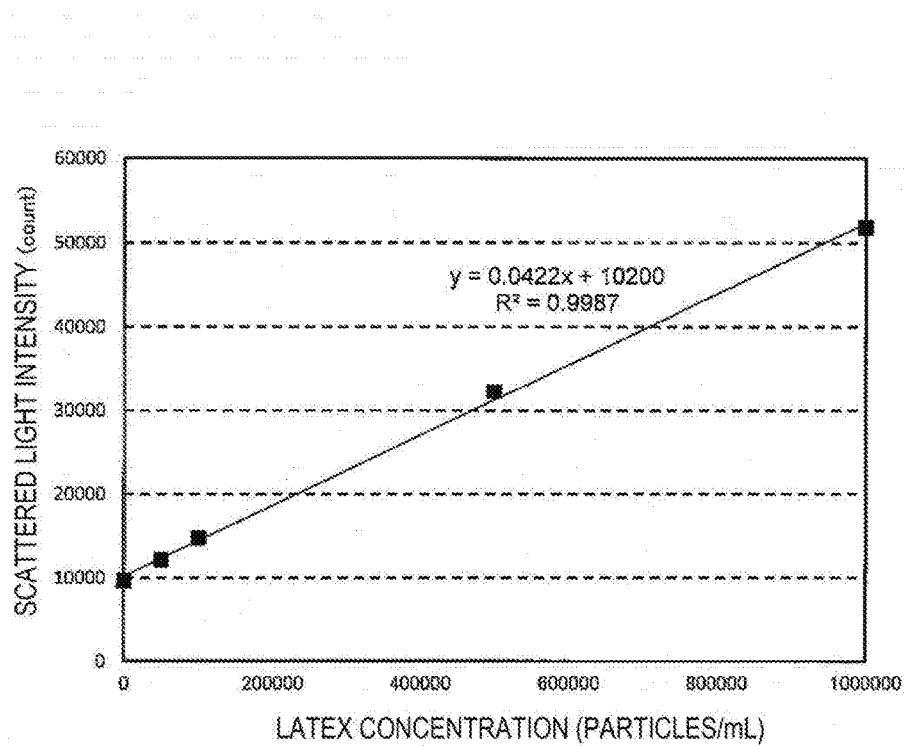

[FIG. 15]
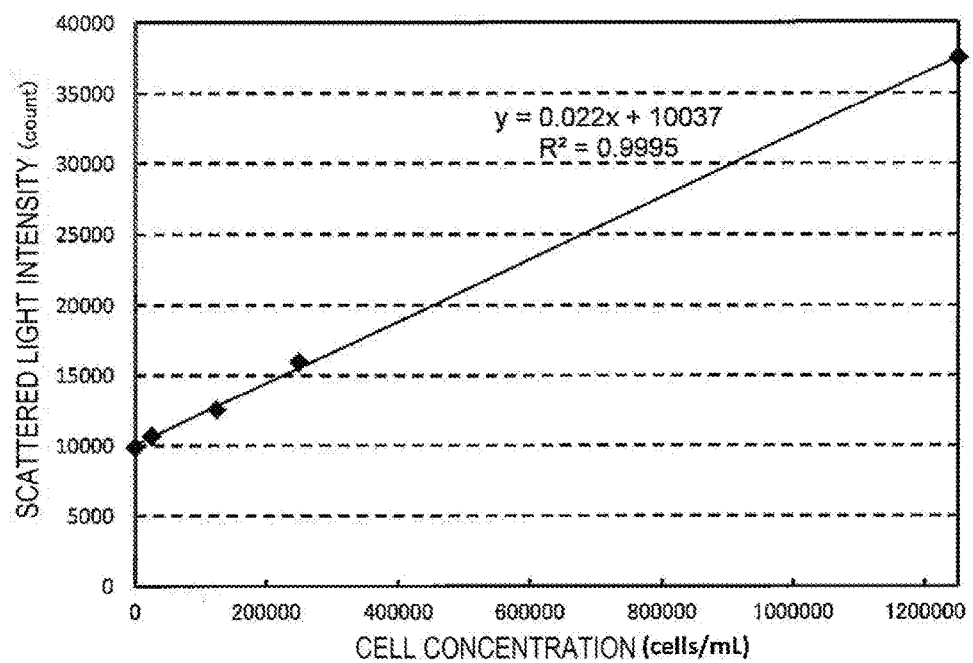

CELL CONCENTRATION ADJUSTMENT DEVICE, AND AUTOMATIC SUBCULTURE SYSTEM USING SAME

TECHNICAL FIELD

The present invention relates to a device which automatically performs cell culture, and in particular to a device which is capable of automatically performing subculture works.

BACKGROUND ART

Conventionally, when anchorage-dependent cells are cultured in a vessel to which the cells are adhered, such as a Petri dish or a flask, almost all the operations have been performed manually. The cell culture operations are complicated and take time, and therefore require enormous personal costs. In addition, since the timings and the like for performing medium exchanges and subculture operations are determined based on experience of the operator, a difference in the survival rate occurs due to a difference in the degree of damage to cells, and thus a difference tends to occur in the state of the cells after subculture operations from operator to operator. Thus, for effecting cell culture in a stable manner at a low cost, a device for automatically performing cell culture operations has been studied and developed.

For example, PTL 1 proposes a cell culture device in which cultured cells are automatically collected to enable efficient subculture. PTL 2 proposes that risk of contamination in culture operations is reduced by using a cell culture device which includes plural culture dishes for culturing cells and a control means for transferring a cell fluid selectively to a certain culture dish.

CITATION LIST

Patent Literatures

PTL 1: JP-A-2008-079554
PTL 2: JP-A-2007-185165

SUMMARY OF INVENTION

Technical Problem

In subculture, operations of collecting cells which have been expanded and cultured in the first time, diluting the cells to an appropriate cell concentration, and re-inoculating the cells, are required. For performing stable subculture, dilution of the collected cells is desirably conducted such that the cell concentration after dilution is constant. In this respect, PTL 1 mentioned above describes that a dilution mechanism for diluting and dispersing cells to be cultured in a medium is provided in a cell culture device, but in the dilution mechanism, cells are not diluted based on measurement of the cell concentration. Although there is no problem in the case where the amount of collected cells is stable for every culture, in the case of use in cell culture, for example, in a regenerative medicine, it is conceivable that the degree of cell growth varies depending on the patient from whom the cells were collected and other factors, and the cell concentration after dilution may be inadequate. Thus, an object of the prevent invention is to provide a device for automatically performing a step in which expanded and cultured cells are diluted to a desired cell concentration and re-inoculated.

Solution to Problem

The present invention provides a device which is capable of automatically performing works of measuring a cell number per unit amount of a cell suspension taken in, taking in a dilution liquid on the basis of the measurement result, and diluting the cell suspension to a desired cell concentration. The gist of the present invention is as follows.

(1) A cell-concentration adjustment device, characterized in that
the device comprises:
an inlet for taking in a cell suspension containing cells at a high concentration;
an outlet for discharging a cell suspension containing cells at a desired concentration which is lower than the concentration at the inlet; and
a flow path which is provided between the inlet and the outlet and is capable of holding a cell suspension, the flow path being provided with:
a liquid delivery pump for causing a cell suspension inside to flow;
a cell-concentration measurement instrument for collecting data related to a cell concentration per unit amount of the cell suspension; and
a dilution-liquid container for holding a dilution liquid which is supplied to the flow path to dilute the cell suspension, and
the device further comprises:
a control unit for controlling at least the liquid delivery pump on the basis of the data obtained by the cell-concentration measurement instrument, wherein the control unit determines, on the basis of the data obtained by the cell-concentration measurement instrument, an amount of the dilution liquid required to bring the cell concentration into the desired concentration, and drives the liquid delivery pump so as to take in the required amount of the dilution liquid into the flow path and mix the cell suspension and the dilution liquid.

(2) The cell-concentration adjustment device according to (1), wherein at least a part of the flow path provided between the inlet and the outlet forms a circulation flow path, the liquid delivery pump and the cell-concentration measurement instrument are provided in the circulation flow path, and the control unit drives the liquid delivery pump to cause the cell suspension and the dilution liquid to repeatedly flow in the circulation flow path until a variation in the data obtained from the cell-concentration measurement instrument becomes a value within a predetermined range, to thereby mix the cell suspension and the dilution liquid.

(3) The cell-concentration adjustment device according to (2), further comprising a buffer tank in the circulation flow path.

(4) The cell-concentration adjustment device according to (1), wherein the control unit drives the liquid delivery pump alternately in a forward direction and a reverse direction, to thereby mix the cell suspension and the dilution liquid.

(5) The cell-concentration adjustment device according to any one of (1) to (4), wherein the cell-concentration measurement instrument measures an intensity of scattered light or transmitted light of light emitted to the cell suspension to collect the data related to the cell concentration as the light intensity, and the control unit calculates the cell concentration by comparing the data with a relationship between cell concentration and light intensity which is determined in advance.

(6) The cell-concentration adjustment device according to any one of (1) to (4), wherein the collection of the data related to the cell concentration by the cell-concentration measurement instrument is performed intermittently or continuously in a state where the cell suspension is flowing.

(7) The cell-concentration adjustment device according to any one of (1) to (4), wherein the control unit is capable of controlling a valve for controlling taking-in of the cell suspension from the inlet and a valve for controlling taking-in of the dilution liquid into the flow path, and the control unit controls the liquid delivery pump and the two valves so as to perform alternately and repeatedly the taking-in of the cell suspension and the taking-in of the dilution liquid.

(8) An automatic subculture system, comprising a first cell culture device for expansion and culture, a cell-concentration adjustment device, and a second cell culture device for subculture, wherein the first cell culture device discharges a cell suspension having a high concentration, the cell-concentration adjustment device dilutes the cell suspension having the high concentration into a uniform cell suspension having a desired cell concentration, the second cell culture device inoculates the diluted cell suspension to perform subculture, and wherein the cell-concentration adjustment device includes an inlet for taking in the cell suspension having the high concentration, an outlet for discharging the cell suspension containing cells at the desired concentration which is lower than the concentration at the inlet, and a flow path which is provided between the inlet and the outlet and is capable of holding a cell suspension, the flow path being provided with a cell-concentration measurement instrument for collecting data related to a cell concentration per unit amount of a cell suspension, and a dilution-liquid container for holding a dilution liquid which is supplied to the flow path to dilute the cell suspension, and the cell-concentration adjustment device further includes a control unit for controlling flow of a cell suspension inside the flow path on the basis of the data obtained by the cell-concentration measurement instrument, wherein the control unit determines, on the basis of the data obtained by the cell-concentration measurement instrument, an amount of the dilution liquid required to bring the cell concentration into the desired concentration, and controls the flow of the cell suspension inside the flow path so that the required amount of the dilution liquid is taken in into the flow path and the cell suspension and the dilution liquid are mixed.

(9) The automatic subculture system according to (8), wherein the control unit controls the flow of the cell suspension inside the flow path of the cell-concentration adjustment device, by using a liquid delivery pump provided in the first cell culture device or the second cell culture device.

(10) A method for diluting a cell suspension containing cells at a high concentration into a desired concentration, the method comprising:

intermittently or continuously measuring an intensity of scattered light or transmitted light of light emitted to the cell suspension in a state where the cell suspension is flowing, to thereby collect data related to a cell concentration as the light intensity;

comparing the obtained data with a relationship between cell concentration and light intensity which is determined in advance to convert the data to a cell concentration; and calculating an amount of a dilution liquid required for dilution to the desired concentration, adding the amount of a dilution liquid to the cell suspension, and mixing the dilution liquid with the cell suspension.

Advantageous Effect of Invention

According to the present invention, regardless of the skill of the operator, expanded and cultured cells can be re-inoculated at a constant concentration, enabling a stable subculture operation. The present invention contributes to realizing stable cell culture at the scene of regeneration medicine and the like.

The Description includes the contents described in Description, Claims and Drawings of Japanese Patent Application Number 2014-148636 which is the basis for claiming priority of this application.

BRIEF DESCRIPTION OF DRAWINGS

FIG. 1 is a schematic diagram showing a first embodiment of the cell-concentration adjustment device of the invention.

FIG. 2 is a schematic diagram of a graph illustrating a variation of a measurement value in a light intensity measurement by a detector 7 during a cell suspension and a dilution liquid are mixed.

FIG. 3 is a schematic diagram showing a second embodiment of the cell-concentration adjustment device of the invention.

FIG. 4 is a schematic diagram showing a third embodiment of the cell-concentration adjustment device of the invention.

FIG. 5 is a schematic diagram showing a cell-concentration adjustment device according to a modified example of the third embodiment.

FIG. 6 is a schematic diagram showing an entire aspect of the subculture system of the invention.

FIG. 7 is a schematic diagram showing a part of a configuration of a first modified example of the subculture system.

FIG. 8 is a schematic diagram showing a part of a configuration of a second modified example of the subculture system.

FIG. 9 is a schematic diagram showing a part of a configuration of a third modified example of the subculture system.

FIG. 10 is a schematic diagram showing a part of a configuration of a fourth modified example of the subculture system.

FIG. 11 is a schematic diagram showing a part of a configuration of a fifth modified example of the subculture system.

FIG. 12 is a schematic diagram showing an entire aspect of a subculture system using an open-type cell culture device.

FIG. 13 is a plot showing a transition of values when scattered light intensity measurements are intermittently performed by a detector provided in a flow cell of a cell-concentration adjustment device to which a cell suspension is supplied.

FIG. 14 is a calibration curve obtained on a relationship between concentration of latex particles having a particle size of 10 μm and scattered light intensity.

FIG. 15 is a calibration curve obtained on a relationship between concentration of Caco-2 cells and scattered light intensity.

DESCRIPTION OF EMBODIMENTS (Cell-Concentration Adjustment Device: First Embodiment)

FIG. 1 is a schematic diagram showing a first embodiment of the cell-concentration adjustment device of the invention. A cell-concentration adjustment device 100 according to the first embodiment has functions to take in a cell suspension containing cells at a high concentration with an unknown cell concentration (number of cells contained in a unit amount of a cell suspension) from an inlet 1, adjust the concentration inside, and discharge a cell suspension containing cells at a desired concentration which is lower than the concentration at the inlet 1 from an outlet 2. The inlet 1 and the outlet 2 are communicated via a flow path 3, a peristaltic pump 4, which is a liquid delivery pump for allowing liquid in the flow path to flow, is provided therein, and a control unit 11 controls at least the peristaltic pump 4. The tube diameter of the flow path does not necessarily have to be uniform, and, for example, a narrow section having a smaller tube diameter maybe provided at least in a part so that aggregated cells are dispersed by a shear force exerted when the cells are passing through the narrow section.

The flow path 3 has at least in a part thereof a section made of an elastic material, and the peristaltic pump 4 crumples the elastic section of the flow path 3 to cause fluid inside the flow path to flow. A peristaltic pump is preferred because driving components such as a blade are not in direct contact with the fluid, and hence the pump can cause the fluid to flow without any contamination and further gives less damage to the dispersed cells. The pump for causing the fluid to flow is not limited to the peristaltic pump, but a pump in which driving components are not in direct contact with fluid therein like a peristaltic pump is preferred. Examples of such a pump include a diaphragm pump and a syringe pump.

A flow cell 5 is provided in a part of the flow path 3, and when a cell suspension is passing through therein, a light intensity is measured as data related to the cell concentration per unit amount. Light is emitted from a light source 6 toward the flow cell 5, and the transmitted light or scattered light thereof or the both are detected by a detector 7. In this embodiment, the light source 6 and the detector 7 constitute the cell-concentration measurement instrument. A relationship between the intensity of the transmitted light or scattered light detected by the detector 7 and the cell concentration is separately determined in advance, and on the basis of the relationship and the light intensity detected by the detector 7, the cell concentration is calculated. The relationship between the intensity of the transmitted light or scattered light and the cell concentration can be obtained, for example, by preparing several cell suspensions of a cell to be cultured with known concentrations, measuring the respective light intensities of the cell suspensions, and creating a calibration curve from the results. Incidentally, the flow rate of the cell suspension passing through the flow cell 5 can be obtained on the basis of the intake from the inlet 1, or on the basis of the volume or the cross-sectional area of the flow cell 5 and the liquid delivery velocity of the peristaltic pump 4. The amount of a dilution liquid required is determined on the basis of the cell concentration and the amount of the cell suspension.

According to the cell concentration measurement based on the light intensity, the cell concentration can be calculated in a state where the cell suspension is flowing. In the case where the cell concentration is calculated in a state where the cell suspension is flowing, the detector 7 may measure the light intensity continuously with no interval, or may measure the light intensity intermittently, that is, with some intervals, preferably with constant intervals. Incidentally, in the cell-concentration adjustment device of the invention, the calculation means for the cell concentration may be another means.

A part of the flow path 3 is branched and connected to a branched flow path 8, and a switching valve 9 is provided at the branching section. The switching valve 9 can switch the flow between the branched flow path 8 and a flow path of the inlet 1 side. A pinch valve is preferably used as the switching valve. Since a pinch valve squashes (pinches) a flow path made of an elastic material from outside to control the flow and is not in direct contact with fluid, the valve can control fluid without contaminating the fluid and the valve itself. The switching valve 9 has a function to switch the two flow paths and can realize the function in combination of two pinch valves, and alternatively, a universal type valve which can be controlled by one actuator to simultaneously and alternately open and close two flow paths may be used. The control unit 11 controls switching of the switching valve by controlling an actuator provided in the valve. The same is applied to other switching valves described later.

A dilution-liquid container 10 containing a dilution liquid is connected to the forward end of the branched flow path 8. The control unit 11 controls at least the peristaltic pump 4, and preferably the switching valve 9 together, to add the dilution liquid to the cell suspension taken in according to a result detected by the detector 7 and further fully stir the cell suspension and the added dilution liquid to make the cell concentration uniform. The control of the peristaltic pump 4, the switching valve 9 and the like by the control unit 11 will be described in detail below.

The control unit 11 drives the peristaltic pump 4, in a state where the switching valve 9 closes the branched flow path 8 and selects the flow path on the inlet 1 side, to take in a neat cell suspension from the inlet 1. The cell suspension taken in is transferred as it is to the flow cell 5. During the cell suspension is passing through the flow cell 5, the light intensity measurement is performed by the detector 7. The control unit 11 calculates the cell concentration from the measurement result, compares the value with a predetermined target value, and then determines an amount of a dilution liquid required through calculation also using the amount of the neat cell suspension taken in.

The control unit 11 then switches the switching valve 9 to a state where the branched flow path 8 side is selected, and drives the peristaltic pump 4 for a certain time to take in the dilution liquid from the dilution-liquid container 10 into the flow path 3. In the flow path 3, the two liquids of the unadjusted cell suspension having a high cell concentration and the dilution liquid are present in a non-uniform state. Next, the control unit 11 switches the direction of rotation of the peristaltic pump 4 between the normal and reverse rotations several times to cause the liquids in the flow path 3 to repeatedly move forward and backward, thereby mixing the two liquids. The flow path 3 has a sufficient space to hold the cell suspension and the dilution liquid including a space for movement of the liquids. Incidentally, mixing of the two liquids can be achieved not only by switching the rotation direction of the peristaltic pump 4 but also, for example, by varying the speed of rotation of the peristaltic pump to vary the flow rate.

FIG. 2 is a schematic diagram of a graph illustrating a variation in the measurement value of the light intensity measurement by the detector 7 during a cell suspension and a dilution liquid are mixed. The measurement value of the light intensity measurement has high amplitude in an initial phase since the cell concentration in the flow path 3 is not uniform, but as the switching of the rotation direction of the peristaltic pump 4 is repeated, gradually the cell concentration becomes uniform to decrease the amplitude, and the measurement value finally converges on a target value, that is, a value of the light intensity corresponding to the predetermined cell concentration. Thus, at a time when the temporal variation in the measurement value of the light intensity measurement is in a predetermined value (the target value ±Δx), preferably at the time when there is no variation, the control unit 11 determines that the liquid in the flow path 3 is uniform. If the converged value is different from the target value, the control unit 11 may repeat again the aforementioned dilution step. The cell suspension in which the cell concentration has been brought into a desired value by the dilution step is discharged from the outlet 2 by driving the peristaltic pump 4.

In the dilution step described above, the taking-in of the cell suspension from the inlet 1 and the taking-in of the dilution liquid from the dilution-liquid container 10 are each performed once, but the control unit 11 may switch the switching valve 9 repeatedly at a shorter time interval so as to alternately take in portions of the cell suspension and the dilution liquid several times. In such a manner, the two liquids are mixed more easily and strain on cells can be reduced, which is preferable.

When the cross-sectional area of the flow path 3 and the like is small with respect to the amount of the cell suspension treated, the movement in the flow path, for example, when liquids are repeatedly moved forward and backward for mixing, takes a time and places a strain on cells. Accordingly, it is preferred that at least the flow path 3 through which a cell suspension passes, and preferably also the flow cell 5, have sufficient cross sectional areas, taking into account the size of the cells treated and the amount of the cell suspension taken in. For example, when the amount of the cell suspension taken in is in the range of 1 mL to 1000 mL, a tube having a diameter of approximately from 1 to 10 mm is preferably used for forming the flow path 3, and a flow cell of 1 to 10 mm square is preferably used for the flow cell 5.

For a tube forming the flow path 3, a material that has no or extremely little influence on cells is preferably used. As an example of such a material, a silicone tube for medical use is mentioned. Although the flow cell 5 may be made of a glass, a flow cell made of an inexpensive resin is preferably used since the flow cell 5 through which cells have once passed can conveniently be disposed together with the flow cell 3.

As a method for measuring the cell concentration, as described above, a method in which the light source 6 emits light toward the flow cell 5, the transmitted light or scattered light or the both are detected by the detector 7 is particularly preferably used since the cell concentration can then be measured in a state where the cell suspension is flowing. However, the measurement method of the cell concentration is not limited thereto, and another method may be adopted. For example, a method in which some kind of observation window is provided in the flow path 3, an image (still image or moving image) is captured by a microscope with a CCD camera, and the cell number is calculated from the image may be used. A measurement in a state where the cell suspension is flowing requires a real time processing, and as long as such a high speed image processing is possible, the method can be adopted as a cell concentration measurement means instead of the light intensity measurement.

In FIG. 1, the switching valve 9 leading to the branched flow path 8, the peristaltic pump 4, and the flow cell 5 are provided in this order in the flow path 3. In this embodiment, the order is not limited to the above and each mechanism can be provided at any position.

Incidentally, since cells settle down when the cell suspension is allowed to stand, the cell-concentration adjustment device of the invention may be used not only as a device for diluting a cell suspension by adding a dilution liquid, but also as a device for simply stirring a cell suspension.

(Cell-Concentration Adjustment Device: Second Embodiment)

FIG. 3 is a schematic diagram showing a second embodiment of the cell-concentration adjustment device of the invention. A cell-concentration adjustment device 101 according to the second embodiment has the same basic configuration as in the first embodiment, but is different in that the flow path after passing through the peristaltic pump 4 is branched and the forward end thereof is returned to the flow path before the passing, thereby configuring the flow path in a cyclic structure. A flow path before passing through the pump is denoted by 3a, a flow path after the passing is denoted by 3b, and a returned flow path after branching is denoted by 12. A switching valve 13 is provided at a branching section to the returned flow path 12 to enable selection between the flow path on the outlet 2 side and the returned flow path 12. The branched flow path 8 to which the dilution-liquid container 10 is connected is placed on the flow path 3a side.

A dilution step by the cell-concentration adjustment device 101 according to the second embodiment is conducted as follows. First, the control unit 11 controls the switching valve 13 to close the returned flow path 12 and select the outlet 2 side flow path and controls the switching valve 9 to close the branched flow path 8 and select the inlet 1 side flow path, and in this state, drives the peristaltic pump 4 to take in a neat cell suspension from the inlet 1. Light intensity measurement and taking-in of a dilution liquid are performed in the same manner as in the first embodiment.

In the second embodiment, mixing of the two liquids of the neat cell suspension having a high cell concentration before adjustment and the dilution liquid is performed by using the flow paths 3a and 3b and the returned flow path 12. The control unit 11 first switches the switching valve 13 to select the returned flow path 12, and in this state, drives the peristaltic pump 4. The cell suspension and the dilution liquid are stirred while circulating in a circulation flow path composed of the returned flow path 12 and the flow paths 3a and 3b, and the cell concentration gradually becomes uniform. During the above, a measurement result similar to that shown in FIG. 2 is obtained by the detector 7. According to the second embodiment, by providing the returned flow path 12, it is possible to mix the liquids without switching the rotation direction of the peristaltic pump 4, whereby effects of enhancing stability of the cell concentration measurement by a light intensity measurement or the like, reducing load on the peristaltic pump 4, simplifying control by the control unit 11, and reducing strain on cells, and other effects can be achieved.

Since at a merging point of the returned flow path 12, the pressure on the pump side of the flow path 3a is lower than the pressure on the inlet 1 side, the liquid flowing in from the returned flow path 12 flows toward the pump side, and does not flow reversely toward the inlet 1 side. However, as required, in the flow path 3a on the inlet 1 side of the merging point of the returned flow path 12, a pinch valve or a check valve for preventing backflow may be provided.

(Cell-Concentration Adjustment Device: Third Embodiment)

FIG. 4 is a schematic diagram showing a third embodiment of the cell-concentration adjustment device of the invention. A cell-concentration adjustment device 102 according to the third embodiment has the same basic configuration as in the second embodiment, but is different in that a buffer tank 14 is provided in the returned flow path 12.

Although the structure of the circulation flow path as in the second embodiment is advantageous in mixing a cell suspension and a dilution liquid as described above, on the other hand, there is a limitation that the mixing has to be performed in the volume of the circulation flow path. Since a neat cell suspension taken in from the inlet 1 has an unknown cell concentration, the amount of a dilution liquid required cannot be estimated in advance, and the total amount of liquid held in the circulation flow path is valuable. It is conceivable to increase the length of the circulation flow path so that the volume of the circulation flow path can treat the maximum amount of liquid that can be assumed. However, when the actual amount of liquid is smaller than the maximum amount of liquid, the efficiency of the mixing is considered to be reduced. In the third embodiment as shown in FIG. 4, this problem is solved by providing the buffer tank 14.

The buffer tank 14 is provided in the middle of the returned flow path 12, and flow paths before and after the buffer tank are denoted by 12a and 12b, respectively. For example, 12a and 12b are connected to the buffer tank 14 so that 12a enters the buffer tank from the top and 12b exits the tank from the bottom. The buffer tank 14 may be opened to the atmosphere, and in this case, it is preferred that a HEPA filter 15 is provided in the middle to prevent contamination by bacteria from the exterior. A switching valve 16 is provided at the merging point of the returned flow path 12b, and enables selection between the inlet 1 side flow path and the peristaltic pump side flow path. As the switching valve, a switching valve of a universal type which can alternately control open and close of two flow paths simultaneously by one actuator is preferably used.

A buffer tank has a purpose of varying the amount of the liquid treated, and does not necessarily have the structure as shown in the drawing, and, for example, a liquid bag made of a stretchable material or a bag folded in a folding paper structure whose volume can be freely changed may be used as a buffer tank. Such a bag may have a structure for releasing air incorporated, or may have a structure in which air is confined in the bag without being released. By providing an outlet of the bag in the lower portion thereof, only liquid can be discharged without mixing of air.

A dilution step by the cell-concentration adjustment device 102 according to the third embodiment is conducted as follows. First, the control unit 11 controls the switching valve 13 to close the outlet 2 side flow path and select the returned flow path 12a side and controls the switching valve 16 to close the returned flow path 12b and select the inlet 1 side flow path, and in this state, drives the peristaltic pump 4 to take in a neat cell suspension from the inlet 1. The liquid taken in is fed to the buffer tank 14. In this time, the neat cell suspension passes through the flow cell and a light intensity measurement is performed. The control unit 11 calculates the cell concentration from the measurement result, compares the value with a predetermined target value, and then determines an amount of a dilution liquid required through calculation also using the amount of the neat cell suspension taken in. The control unit 11 then switches the switching valve 9 to take in a dilution liquid from the dilution-liquid container 10.

After the switching valve 16 is switched so as to select the returned flow path 12b, the neat cell suspension taken in and the dilution liquid are mixed by circulating in the circulation flow path composed of the returned flow paths 12a and 12b including the buffer tank 14 and the flow paths 3a and 3b. After the switching valve 13 is switched so as to select the outlet 2 side flow path, the peristaltic pump 4 can be driven to discharge the cell suspension brought into a desired cell concentration from the outlet 2.

In the circulation flow path, liquid enters the buffer tank 14 from the top and drops down therein, and in the other flow paths, liquid passes through thin tubes, whereby mixing is achieved. The volume of the buffer tank 14 and the volume of each flow path can be appropriately determined taking into account the efficiency of stirring in the buffer tank 14 and the other flow paths and an amount of the liquid assumed to be treated. As an example, the following case is mentioned. That is, in a case where the amount of the liquid treated is in the range of approximately from 120 mL to 180 mL, the volume of the circulation flow path is made 100 mL, and the volume of the buffer tank 14 is made 100 mL. When the buffer tank 14 is provided, since air can be removed from the inside of the circulation flow path, an advantage of stabilizing the cell concentration measurement can also be obtained.

FIG. 5 is a schematic diagram showing a cell-concentration adjustment device 103 according to a modified example of the third embodiment. In the embodiments described above, taking-in of a dilution liquid was performed by the identical peristaltic pump 4 which is used for taking in a cell suspension and mixing a cell suspension and a dilution liquid. Although a flow rate of the pump which is high to some extent is efficiency for taking in and mixing a suspension liquid, a pump having a high flow rate is not so suitable for detail control on taking in a dilution liquid. In addition, since the peristaltic pump 4 itself has a large fluctuation in the flow rate, the peristaltic pump 4 is not so suitable for injection of a minute amount of liquid. Thus, the cell-concentration adjustment device 103 according to the modified example shown in FIG. 5 is configured to perform addition of a dilution liquid by a microvolume pump 18 which is newly provided. As the microvolume pump 18, for example, a diaphragm pump, a syringe pump, and the like can be used. In this modified example, when the addition of a dilution liquid is performed by injecting the liquid into the buffer tank 14, the switching valve 9, which is provided in the third embodiment, is not required.

(Subculture System Using Cell-Concentration Adjustment Device)

A subculture system using the cell-concentration adjustment device of the invention will be hereinunder described. When the inlet and the outlet are closed, the cell-concentration adjustment device of the invention forms a closed system without contamination by bacteria from the exterior, and therefore when this device is connected with a closed-type cell culture device, the entire system can be made a closed system. An example of connection with a closed-type cell culture device will be described below.

FIG. 6 is a schematic diagram showing an entire aspect of the subculture system of the present invention. In a closed-type cell culture device 200, a culture vessel 19 is connected to a feeding bag 20 and a collection bag 21 to form a single closed system. By conducting culture in a closed system, safe and reliable culture can be conducted without contamination by bacteria from the exterior. A plural number of the feeding bag 20 may be provided, and the individual flow paths 22 connected to the respective bags are arranged in parallel. All the flow paths 22 lead to a common flow path 23 and any of the feeding bags 20 can be selected by a switching valve 24 provided on the individual flow paths 22. Here, a cell suspension 20a, a medium 20b, a stripping liquid 20c, and a sterilized air 20d are respectively contained in the feeding bags, but the contents of the feeding bags are not limited thereto. Incidentally, the sterilized air is used for pushing a previously contained liquid from the rear to discharge the liquid. Instead of the feeding bag, a HEPA filter may be connected to allow the system to be opened to the atmosphere. Contamination by bacteria can be prevented by the HEPA filter.

A plural number of the collection bag 21 may also be provided, and then, the individual flow paths 25 are arranged in parallel, all the flow paths 25 lead to a common flow path 26, and any of the collection bags 21 can be selected by a switching valve 27 provided on the individual flow paths 25. Here, a waste liquid 21a and a cell suspension 21b are respectively contained in the collection bags, but the contents of the collection bags 21 are not limited thereto.

By driving a peristaltic pump 28 while selecting any of the feeding bags 20 and any of the collection bags 21 by the switching valves 24 and 27, liquid delivery required for the culture is performed. After the cell suspension 20a is inoculated into the culture vessel 19, culture is conducted while regularly exchanging the medium. After the culture, cells are stripped from the culture vessel 19 by the stripping liquid 20c to collect the cells into the collection bag 21b.

Closed-type cell culture devices and a cell-concentration adjustment device are connected, and subculture is conducted as follows. Two culture devices of a closed-type cell culture device 200 for performing the first expansion and culture and a closed-type cell culture device 210 for performing culture after passage are present. The two culture devices have the same basic configuration. The culturing amount of the latter is more, and hence for the latter, a vessel having a larger area may be used, or plural culture vessels may be provided and connected in parallel in which liquid is delivered while switching the culture vessels by a switching valve not shown.

The collection bag 21b for containing a cell suspension of the culture device 200 and the inlet 1 of the cell-concentration adjustment device 102 are connected via a connection flow path 30, and the outlet 2 of the cell-concentration adjustment device 102 and the feeding bag 20a for containing a cell suspension of the culture device 210 are connected via a connection flow path 31. Here, the cell-concentration adjustment device 102 is one according to the second embodiment, but one according to the other embodiments can be used.

The cell-concentration adjustment device 102 takes in a cell suspension which is treated as a neat cell suspension from the collection bag 21b. The amount of cells collected is not constant depending on the result of the expansion and culture, it is desired that the peristaltic pump 4 is driven for a long time to feed the entire amount into the buffer tank 14. In addition, light intensity measurement by the detector 7 may be performed also during the taking-in to measure a time period from the time when the liquid reaches there to the time when running out of the liquid occurs, thereby calculating from the time period the amount of the liquid taken in.

A cell suspension which has been uniformly diluted in the cell-concentration adjustment device 102 according to the step as described above so as to have a target cell concentration is fed to the feeding bag 20a for a cell suspension in the culture device 210. The entire amount of the cell suspension held in the cell-concentration adjustment device 102 may be delivered, or light intensity measurement may be performed by the detector 7 to calculate the amount of the liquid to be delivered on the basis of the measurement result. The culture device 210 to which the cell suspension diluted to the target cell concentration has been delivered conducts culture in the same manner as the culture device 200.

(Modified Example and Application Example of Subculture System)

In the subculture system described above using FIG. 6, the cell suspension is transferred from the former device to the latter device after the operation in the former device is completed, but the cell suspension may be directly transferred between devices for saving time. In such a case, in a configuration in which two peristaltic pumps are used in series in one flow path, if the delivery velocities of the two pumps are not equal, a problem occurs in the internal pressure of the flow path between the peristaltic pumps, and therefore it is preferred that a buffer area is provided between the two pumps. The buffer area can freely change the volume without changing the internal pressure, and, for example, a liquid bag made of a stretchable material, a bag body folded in a folding paper structure having a freely changeable volume, a structure opened to the atmosphere such as the buffer tank 14, and the like can be used as the buffer area. In a structure as shown in FIG. 6, the collection bag 21b of the culture device 200 and the feeding bag 20a of the culture device 210 play a role of the buffer area.

(Subculture System: First Modified Example)

FIG. 7 is a schematic diagram showing a part of a configuration of a first modified example of the subculture system. In this configuration, a cell suspension discharged from a cell culture device for expansion and culture is directly fed into a cell-concentration adjustment device. A cell culture device 201 has the same basic configuration as in the cell culture device 200, but is different therefrom in that a collection bag of a cell suspension is not provided and the device is connected to a cell-concentration adjustment device 104 via a connection flow path 32. The cell-concentration adjustment device 104 has a configuration in which the buffer tank 14 is placed between the peristaltic pump 4 and the inlet 1. A flow path on the inlet 1 side is denoted by 3a1 and a flow path on the pump side is denoted by 3a2, and 3a1 enters the buffer tank 14 from the top and 3a2 exits the tank from the bottom. A flow path 3b after passing through the peristaltic pump 4 is divided and one of the divided flows is the returned flow path 12, and returned to the top of the buffer tank 14. In this configuration, the switching valve at the merging point of the returned flow path 12 is not necessary. The switching valve 13 is provided at the division between the flow path 3b and the returned flow path 12. The branched flow path 8 which leads to the dilution-liquid container 10 is provided between the buffer tank 14 and the peristaltic pump 4. A cell dispersion discharged from the culture device 201 is fed to the buffer tank 14 of the cell-concentration adjustment device 104 by the peristaltic pump 28 of the cell culture device 201. Since the cell-concentration adjustment device 104 is not provided with a buffer area in the flow path after passing through the peristaltic pump 4, a cell suspension having a cell concentration adjusted by the cell-concentration adjustment device 104 is fed to the cell suspension feeding bag 20a of the cell culture device 210 for subculture via the flow path 31.

(Subculture System: Second Modified Example)

FIG. 8 is a schematic diagram partially showing a configuration of a second modified example of the subculture system. In this configuration, a cell culture device for subculture 211 is not provided with a cell suspension feeding bag. A cell-concentration adjustment device 105 has a configuration in which the buffer tank 14 is provided between the peristaltic pump 4 and the outlet 2. A flow path on the pump side is denoted by 3b1 and a flow path on the outlet 2 side is denoted by 3b2. 3b1 enters the buffer tank 14 from the top and 3b2 exits the buffer tank 14 from the bottom. The flow path 3b2 is divided and one of the divided flows is the returned flow path 12 and is returned to the flow path 3a before passing through the peristaltic pump. The switching valve 16 is provided at the merging point. The branched flow path 8 leading to the dilution-liquid container 10 is placed on the flow path 3a side. In this configuration, a switching valve at the branching section of the returned flow path 12 from the flow path 3b2 is not necessary. Since no buffer area is present between the flow path 3b2 and the peristaltic pump 28 of the culture device for subculture 211 and the liquid cannot escape, even if a switching valve is not present at the branching section of the returned flow path 12, backflow does not occur when driving the peristaltic pump 4. However, when a large amount of air is present in this space, the air expands and possibly in turn causes a backflow toward the returned flow path side from the outlet 2, and therefore a pinch valve or a check valve for preventing backflow may be provided between the branching to the returned flow path and the outlet 2 for preventing backflow. Incidentally, the collection bag 21b is provided in the cell culture device for expansion and culture 200 and functions as a buffer area against the cell-concentration adjustment device 105. A cell suspension having a cell concentration adjusted by the cell-concentration adjustment device 105 is transferred by driving the peristaltic pump 28 of the culture device for subculture 211 and is directly inoculated in the culture device 211.

(Subculture System: Third Modified Example)

FIG. 9 is a schematic diagram showing a part of a configuration of a third modified example of the subculture system. In this configuration, no buffer area is provided in any of a cell culture device for expansion and culture, a cell-concentration adjustment device and a cell culture device for subculture. A cell-concentration adjustment device 106 is provided with the buffer tank 14 between the flow paths 3A and 3B which connect the inlet 1 and the outlet 2, and the peristaltic pump 4 is provided in the middle of the returned flow path 12. The returned flow path 12 enters the buffer tank 14 from the top and thus a switching valve is not necessary. The branched flow path 8 leading to the dilution-liquid container 10 is provided before the peristaltic pump 4 in the middle of the returned flow path 12. In this configuration, a cell suspension fed from the cell culture device for subculture 211 to the buffer tank 14 is circulated in the circulation flow path by driving the peristaltic pump 4. As required, a valve may be provided in the flow path 3A connecting the inlet 1 and the buffer tank 14, or in the flow path 3B after the branching to the returned flow path 12 and before the outlet 2. Feeding of a cell suspension to the cell culture device for subculture 211 is performed by driving the peristaltic pump 28 in the cell culture device 211.

(Subculture System: Fourth Modified Example)

FIG. 10 is a schematic diagram showing a part of a configuration of the fourth modified example of the subculture system. A cell-concentration adjustment device 107 used here does not have a returned flow path, and mixing is achieved by causing liquid to flow forward and backward. The cell-concentration adjustment device 107 itself does not have a peristaltic pump, and causes liquid to flow using a peristaltic pump in culture devices. In a state where the switching valve 27 in the culture device for expansion and culture 201 selects the flow path 32, the peristaltic pump 28 of the culture device 201 is driven to feed a cell suspension to the cell-concentration adjustment device 107. Taking-in of a dilution liquid is performed by driving the peristaltic pump 28 in a reversed direction of rotation in a state where the branched flow path side is opened by switching the switching valve 9. The switching valve 9 is switched back to the initial state, and the rotation direction of the peristaltic pump is switched several times to achieve mixing. The cell suspension having a cell concentration adjusted is delivered to the feeding bag 20 of the cell culture device for subculture 210 by the peristaltic pump of the cell culture device 201. Then, the switching valve 27 on the cell culture device 201 side is switched to close the connection flow path 32.

(Subculture System: Fifth Modified Example)

FIG. 11 is a schematic diagram showing a part of a configuration of a fifth modified example of the subculture system. In this configuration, the forth modified example is further modified, and all the transfers of the cell suspensions between a cell culture device and a cell-concentration adjustment device are performed in a direct manner. A cell-concentration adjustment device 108 is provided with a branched flow path 34 on each of the inlet 1 side and the outlet 2 side of the flow path 3, and has a configuration in which the two branched flow paths are connected to a common flow path 36 opened to the atmosphere. The common flow path 36 is switchable by a switching valve 35, and an HEPA filter 37 is connected to the common flow path to prevent contamination by bacteria from the exterior. First, the peristaltic pump 28 is driven in a state where the switching valve 35 opens the outlet 2 side and the switching valve 27 of the cell culture device for expansion and culture 201 selects the connection flow path 32, to thereby feed a cell suspension to the cell-concentration adjustment device 108. Light intensity measurement is performed by the detector 7 and, as required, the switching valve 9 is switched to open the branched flow path side, and the rotation direction of the peristaltic pump 28 is reversed to take in a dilution liquid. Then, the switching valve 27 on the cell culture device 201 side is switched to close the connection flow path 32. A cell suspension having a cell concentration adjusted is delivered to the cell culture device 211 by driving the peristaltic pump 28 of the cell culture device 211 in a state where the branched flow path 34 on the outlet 2 side is closed by switching the switching valve 35.

(Subculture System: Application Example)

Although the above descriptions were made on the assumption of the subculture system using closed-type cell culture devices, the subculture system of the present invention can use not only a closed-type, but also an open-type cell culture device. An open-type cell culture device is a device for conducting culture in a culture vessel which is not closed, for example, while the medium is exchanged by removing a lid of the culture vessel in the same manner as in cell culture by a general procedure. Although the risk of contamination by bacteria is increased, such a device is advantageous in a higher degree of freedom in liquid handling. The risk of contamination by bacteria can be reduced by placing the device in a clean room.

FIG. 12 is a schematic diagram showing an entire aspect of a subculture system using open-type cell culture devices. An open-type cell culture device 300 includes a culture vessel 38 which is not closed, and a feeding-liquid container 39 and a collection-liquid container 40 which are also not closed. As a feeding liquid, a cell suspension 39a, a medium 39b, and a stripping liquid 39c may be mentioned, and as a collection liquid, a waste liquid 40a and a cell suspension 40b may be mentioned. The liquids are sucked and discharged by a dispensing mechanism 41. The culture vessel is placed in an incubator 42 and culture is conducted in an environment suitable for the culture.

A taking-in flow path 43 and a taking-out flow path 44 are respectively connected to the inlet 1 and the outlet 2 of the cell-concentration adjustment device 102, and respectively extended into the collection-liquid container 40b of the cell culture device for expansion and culture 300 and into the feeding liquid container 39a of the culture device for subculture 310. A cell suspension which has been cultured and collected in the cell culture device for expansion and culture 300 is collected into the collection-liquid container 40b by the dispensing mechanism 41. The cell-concentration adjustment device takes in the cell suspension from the taking-in flow path 43, adjusts the cell concentration, and then discharges the resulting cell suspension from the taking-out flow path 44 into the feeding-liquid container 39a of the cell culture device for subculture 310.

In the case where the cell-concentration adjustment device 106, 107, or 108 is used instead of the cell-concentration adjustment device 102 in a subculture system using open-type cell culture devices, since the cell-concentration adjustment device does not have an ability of auto-sucking and auto-discharging liquid, the device cannot be used as it is as an open-type culture device. A separate means for allowing liquid to be fed to and to be discharged from the buffer tank 14 is required. In the case where open-type culture devices are connected, the cell-concentration adjustment device 100 or 103 is preferably used. Alternatively, the cell-concentration adjustment device 104 or 105 can be used as long as one of the cell culture devices is of a closed-type.

EXAMPLES

1. Preparation of Cell Dispersion

In 9 mL of a culture solution for Caco-2 cells having 10% Fetal Bovine Serum (FBS) added thereto, $4.6 \times 10^6$ cells of Caco-2 (human large bowel cancer cell strain) cryopreserved at $-80°$ C. was suspended, and the entire amount of the suspension was inoculated and cultured in a vessel for expansion and culture having a bottom surface area of 78.5 $cm^2$ of a cell culture device, and 2 days later, a 80% confluent state was reached. Then, the cells were washed with 3 mL of PBS and stripped by introducing 2 mL of 0.25% trypsin-1 mM EDTA, followed by standing at 37° C. for 4 minutes, the trypsin was deactivated by introducing 3 mL of the culture solution, and the culture solution containing the stripped cells was collected.

5 mL of the culture solution containing the collected cells was supplied to a cell-concentration adjustment device having the same configuration as shown in FIG. 3. Flow paths in the cell-concentration adjustment device were formed of a silicone tube having an inner diameter of 3.15 mm, and the total length thereof was 520 mm. A thin tube of 0.7 mm inner diameter×1 mm length was provided in a part of the flow paths so as to easily disperse the cells. In addition, a flow cell of 5 mm square was used for light intensity measurement. When scattered light intensity measurements (wavelength: 700 nm, measurement angle: 20°) were performed intermittently by a detector while driving a peristaltic pump so as to cause approximately 10 times of circulation in the circulation flow path, it was observed that the measurement value converged with time (FIG. 13). When the state of the cell suspension was visually checked, the cells were dispersed at the same degree with a dispersion in which cells were dispersed manually by pipetting the same sample approximately 10 times.

2. Cell Concentration Measurement by Scattered Light Intensity Measurement (1) Simulation by Latex Beads Latex particles with a particle diameter of 10 μm (manufactured by Polysciences, Inc.) were used to verify how degree the concentration measurement based on scattered light intensity measurement reproduced the actual concentration as compared with a value obtained by a cell counter. First, several latex particle suspensions having known concentrations were prepared, each suspension was put into a cell-concentration adjustment device having the same configuration as shown in FIG. 3, and scattered light intensity measurements were performed by a detector provided in a flow cell to create a calibration curve (FIG. 14). Next, a latex particle suspension having a concentration of $5.0 \times 10^5$ particles/mL was prepared, a scattered light intensity measurement was performed 6 times, and the concentration was calculated by comparing each measurement value with the calibration curve. The average concentration was $5.24 \times 10^5$ particles/mL, and the standard deviation was $0.0097 \times 10^5$ particles/mL, and the reproducibility was RSD=0.19%. On the other hand, in a measurement by a cell counter, a mixture in which the same latex particle suspension and trypan blue dye were sufficiently mixed by pipetting was measured. When the measurement was performed 6 times, the average concentration was $4.59 \times 10^5$ particles/mL, the standard deviation was $0.336 \times 10^5$ particles/mL, and the reproducibility was RSD=7.32%.

(2) Scattered Light Intensity Measurement Using Caco-2 Cells

Several Caco-2 cell suspensions having known concentrations were prepared, and scattered light intensity measurements were performed in the same manner as in the above (1) to create a calibration curve (FIG. 15).

3. Cell Concentration Adjustment and Subculture

A Caco-2 cell suspension having an unknown concentration was prepared and put into a cell-concentration adjustment device having the same configuration as shown in FIG. 3, and a scattered light intensity measurement was performed by a detector provided in a flow cell. When the obtained value was compared with the calibration curve obtained in the above 2(2), the concentration of the cell suspension was determined to be $1.2 \times 10^6$ cells/mL. On the basis of the value and a known growing curve of Caco-2 cells, the concentration of the re-inoculated cells required to achieve 50% confluent after 2 days in two subculture vessels having a bottom area of 78.5 $cm^2$ was calculated by a control unit, and 15 mL of a dilution liquid was supplied. The dilution liquid was sufficiently mixed with the cell suspension, and the mixture was supplied to a cell culture device for subculture connected to the cell-concentration adjustment device. In the cell culture device, 10 mL each of the cell suspension having the adjusted concentration was inoculated into the two culture vessels.

For checking the activity of the cells after subculture, the re-inoculated cells were cultured for 2 days and examined for the growth rate and the survival rate. In the results, the cell concentration after 2 days was $3.8 \times 10^6$ cells/mL, and the survival rate of the cells was 96 to 97% (n=4). The apparent occupancy by cells was 50% confluent.

All publications, patents and patent applications cited herein are incorporated herein by reference in its entirety.

REFERENCE SIGNS LIST

1: Inlet, 2: Outlet, 3: Flow path, 4: Peristaltic pump, 5: Flow cell, 6: Light source, 7: Detector, 8: Branched flow path, 9: Switching valve, 10: Dilution-liquid container, 11: Control unit, 12: Returned flow path, 13: Switching valve, 14: Buffer tank, 15: HEPA Filter, 16: Switching valve, 17: Dilution-liquid flow path, 18: Microvolume pump, 19: Culture vessel, 20: Feeding bag, 21: Collection bag, 22: Individual flow path, 23: Common flow path, 24: Switching valve, 25: Individual flow path, 26: Common flow path, 27: Switching valve, 28: Peristaltic pump, 29: Incubator, 30: Connection flow path, 31: Connection flow path, 32: Connection flow path, 33: Connection flow path, 34: Branched flow path, 35: Switching valve, 36: Common flow path, 37: HEPA Filter, 38: Culture vessel, 39: Feeding-liquid container, 40: Collection-liquid container, 41: Dispensing mechanism, 42: Incubator, 43: Taking-in flow path, 44: Taking-out flow path, 100-108: Cell-concentration adjustment device, 200 and 201: Cell culture device (for expansion and culture), 210 and 211: Cell culture device (for subculture), 300: Open-type cell culture device (for expansion and culture)

The invention claimed is:

1. A cell-concentration adjustment device, the device comprising:
   an inlet for taking in a cell suspension containing cells at a first concentration;
   an outlet for discharging a cell suspension containing cells at a second, desired concentration which is lower than the first concentration at the inlet; and
   a flow path which is provided between the inlet and the outlet and is capable of holding a cell suspension, the flow path comprising
      a liquid delivery pump for causing a cell suspension inside to flow;
      a cell-concentration measurement instrument for collecting data related to a cell concentration per unit amount of the cell suspension; and
      a dilution-liquid container for holding a dilution liquid which is supplied to the flow path to dilute the cell suspension,
   wherein the cell-concentration adjustment device further comprises
   a controller configured to control at least the liquid delivery pump on the basis of the data obtained by the cell-concentration measurement instrument,
   wherein the controller determines, on the basis of the data obtained by the cell-concentration measurement instrument, an amount of the dilution liquid required to bring the cell concentration into the desired concentration, and drives the liquid delivery pump so as to take in the required amount of the dilution liquid into the flow path and mix the cell suspension and the dilution liquid, and
   wherein at least a part of the flow path provided between the inlet and the outlet forms a circulation flow path, the liquid delivery pump and the cell-concentration measurement instrument are provided in the circulation flow path, and the controller drives the liquid delivery pump to cause the cell suspension and the dilution liquid to repeatedly flow in the circulation flow path until a variation in the data obtained from the cell-concentration measurement instrument converges to a value within a predetermined range, to thereby mix the cell suspension and the dilution liquid.

2. The cell-concentration adjustment device according to claim 1, further comprising a buffer tank in the circulation flow path.

3. The cell-concentration adjustment device according to claim 1, wherein the control unit drives the liquid delivery pump alternately in a forward direction and a reverse direction, to thereby mix the cell suspension and the dilution liquid.

4. The cell-concentration adjustment device according to claim 1, wherein the cell-concentration measurement instrument measures an intensity of scattered light or transmitted light of light emitted to the cell suspension to collect the data related to the cell concentration as the light intensity, and the controller calculates the cell concentration by comparing the data with a relationship between cell concentration and light intensity which is determined in advance.

5. The cell-concentration adjustment device according to claim 1, wherein the collection of the data related to the cell concentration by the cell-concentration measurement instrument is performed intermittently or continuously in a state where the cell suspension is flowing.

6. The cell-concentration adjustment device according to claim 1, wherein the controller is configured to control a valve for controlling taking-in of the cell suspension from the inlet and a valve for controlling taking-in of the dilution liquid into the flow path, and the controller controls the liquid delivery pump and the two valves so as to alternately and repeatedly perform the taking-in of the cell suspension and the taking-in of the dilution liquid.

7. An automatic subculture system, comprising:
   a first cell culture device for expansion and culture;
   a cell-concentration adjustment device; and
   a second cell culture device for subculture,
   wherein the first cell culture device discharges a cell suspension having a first concentration, the cell-concentration adjustment device dilutes the cell suspension having the first concentration into a uniform cell suspension having a second, desired cell concentration, the second cell culture device inoculates the diluted cell suspension to perform subculture, and
   wherein the cell-concentration adjustment device includes an inlet for taking in the cell suspension having the first concentration, an outlet for discharging the cell suspension containing cells at the second, desired concentration which is lower than the first concentration at the inlet, and a flow path which is provided between the inlet and the outlet and is capable of holding a cell suspension,
   wherein the flow path being provided with a cell-concentration measurement instrument for collecting data related to a cell concentration per unit amount of a cell suspension, and a dilution-liquid container for holding a dilution liquid which is supplied to the flow path to dilute the cell suspension,
   wherein the cell-concentration adjustment device further comprises a controller configured to control a flow of a cell suspension inside the flow path on the basis of the data obtained by the cell-concentration measurement instrument using a liquid delivery pump provided in the first cell culture device or the second cell culture device, wherein the controller determines, on the basis of the data obtained by the cell-concentration measurement instrument, an amount of the dilution liquid required to bring the cell concentration into the second, desired concentration, and controls the flow of the cell suspension inside the flow path so that the required amount of the dilution liquid is taken in into the flow path and the cell suspension and the dilution liquid are mixed, and wherein at least a part of the flow path provided between the inlet and the outlet forms a circulation flow path, the liquid delivery pump and the cell-concentration measurement instrument are provided in the circulation flow path, and the controller drives the liquid delivery pump to cause the cell suspension and the dilution liquid to repeatedly flow in the circulation flow path until a variation in the data obtained from the cell-concentration measurement instrument converges to a value within a predetermined range, to thereby mix the cell suspension and the dilution liquid.

8. A method for diluting a cell suspension containing cells at a first concentration into a second, desired concentration, the method comprising:

receiving, via an inlet, a cell suspension containing cells at a first concentration;

intermittently or continuously measuring an intensity of scattered light or transmitted light of light emitted to the cell suspension in a state where the cell suspension is flowing, to thereby collect data related to a cell concentration as the light intensity;

comparing the obtained data with a relationship between cell concentration and light intensity which is determined in advance to convert the data to a cell concentration; and calculating an amount of a dilution liquid required for dilution to the desired concentration, adding the amount of a dilution liquid to the cell suspension, and mixing the dilution liquid with the cell suspension; and discharging, via an outlet, a cell suspension containing cells at a second, desired concentration which is lower than the first concentration at the inlet, wherein said mixing the dilution liquid with the cell suspension further comprises driving a liquid delivery pump to cause the cell suspension and the dilution liquid to repeatedly flow in a circulation flow path until a variation in the measured cell-concentration converges to a value within a predetermined range, to thereby mix the cell suspension and the dilution liquid.

* * * * *